US00PP17716P3

(12) United States Plant Patent

Kerley et al.

(10) Patent No.: US PP17,716 P3

(45) Date of Patent: May 8, 2007

(54) *PRIMULA* PLANT NAMED 'KERBELMILK'

(50) Latin Name: *Primula vulgaris*
Varietal Denomination: Kerbelmilk

(76) Inventors: David W. Kerley, Bethany, 49 Station Road, Over, Cambridge (GB), CB4 5NJ; Priscilla G. Kerley, Bethany, 49 Station Road, Over, Cambridge (GB), CB4 5NJ ( * ) Notice: Subject to any disclaimer, the term of this patent is extended or adjusted under 35 U.S.C. 154(b) by 0 days.

(21) Appl. No.: 11/242,256

(22) Filed: Oct. 3, 2005

(65) Prior Publication Data

US 2007/0079410 P1 Apr. 5, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell

(74) *Attorney, Agent, or Firm*—Donald D. Jeffery

(57) ABSTRACT

A new and distinct cultivar of *Primula* plant named 'Kerbelmilk,' characterized by its upright, compact, and uniform plant habit; large, double, nonfragrant and cream-colored flowers that are held upright on strong and erect peduncles; early flowering in natural season; fast production suitable for 9 cm to 12 cm pots; an enlarged calyx which forms a green collar around the flower; and tolerance to low temperatures.

1 Drawing Sheet

Botanical designation: *Primula vulgaris.*
Cultivar denomination: 'Kerbelmilk'.

BACKGROUND OF THE INVENTION

The present invention relates to a new and distinct cultivar of *Primula* plant, botanically known as *Primula vulgaris,* commonly known as primrose, and hereinafter referred to by the cultivar name 'Kerbelmilk.'

The new *Primula* is a product of a planned breeding program conducted by the inventors in Over, Cambridge, United Kingdom. The objective of the breeding program was to create new, compact pot-type *Primula* cultivars with numerous double flowers, short peduncles, and attractive leaf and flower coloration.

The new *Primula* originated from a cross-pollination made by the inventors in Over, Cambridge, United Kingdom, of two unnamed and unpatented proprietary *Primula vulgaris* seedling selections in March 2001. The new cultivar, 'Kerbelmilk,' was discovered and selected by the inventors as a flowering plant within the progeny of the stated cross in a controlled environment in Over, Cambridge, United Kingdom, in February 2002. The breeding program also produced several other new cultivars disclosed in pending applications, namely, Ser. No. 11/046,000 for 'Kerbelbut', now U.S. Plant Pat. No. 16,373; Ser. No. 11/045,999 for 'Kerbelcrem'; Ser. No. 11/045,997 for 'Kerbelnec', now U.S. Plant Pat. No. 16,365; and Ser. No. 11/046,033 for 'Kerbelpice', now U.S. Plant Pat. No. 16,598. All of these applications were filed in the Patent and Trademark Office Jan. 28, 2005.

The new cultivar was first asexually propagated by the inventors by tissue culture in the summer of 2002 in Enniscorthy, Ireland, and that and subsequent propagations have shown that the unique features of this new *Primula* are stable and reproduced true-to-type in successive generations.

SUMMARY OF THE INVENTION

Plants of the cultivar 'Kerbelmilk' have not been observed under all possible environmental conditions. The phenotype may vary somewhat with variations in environment, such as temperature, light intensity, day length, and fertility level without, however, any variance in genotype.

The following traits have been repeatedly observed, and are determined to be the unique characteristics of 'Kerbelmilk.' These characteristics, in combination, distinguish 'Kerbelmilk' as a new and distinct cultivar:

1. Upright, compact, and uniform plant habit.
2. Large, double, light-yellow-to-cream-colored flowers that are held upright on strong and erect peduncles.
3. Freely flowering habit.
4. Early to flower in natural season.
5. Well suited to production in 9–12 cm pots, and a fast producer.
6. An enlarged calyx produces an attractive green collar which surrounds the flower.
7. The new cultivar is hardy in the United Kingdom.

Plants of 'Kerbelmilk' differ from plants of both the female and male parents by their double flowers, compact plant habit, and sterile nature.

In comparison to the unpatented *Primula vulgaris* 'Dawn Ansell', based on side-by-side comparisons conducted in Over, Cambridge, United Kingdom, plants of 'Kerbelmilk' are distinguished from plants of 'Dawn Ansell' by their larger, cream-colored flowers compared to the white flowers of 'Dawn Ansell', enlarged calyx, and thicker, stronger peduncles.

In comparison to applicants' pending application for 'Kerbelcrem,' referred to above, 'Kerbelmilk' differs from 'Kerbelcrem' by its enlarged calyx, smaller flower diameter, light yellow flowers, and lack of fragrance.

BRIEF DESCRIPTION OF THE PHOTOGRAPH

The accompanying colored photograph illustrates the overall appearance of the new cultivar, showing the colors as true as it is reasonably possible to obtain in colored reproductions of this type.

The photograph at the top of the sheet comprises a top perspective view of a typical flowering plant of 'Kerbelmilk' grown in an 11 cm container.

The photograph at the bottom of the sheet is a close-up view of a typical flower of 'Kerbelkmilk.'

DETAILED BOTANICAL DESCRIPTION

The aforementioned photographs, following observations and measurements describe plants grown in Over, Cambridge, United Kingdom, in a glass-covered greenhouse and under commercial production practices during the spring. Plants were about four to five months old when the photographs were taken. The description of the plants was made approximately five weeks later. The plants described were grown under daytime temperatures ranging from 15° C. to 25° C. and nighttime temperatures ranging from 15° C. to 20° C. In the following description, color references are made to The Royal Horticultural Society Colour Chart, 1995 Edition, except where general terms or ordinary dictionary significance are used.

Botanical classification: *Primula vulgaris* cultivar 'Kerbelmilk'.

Parentage:

*Female, or seed, parent.*—Unnamed and unpatented proprietary *Primula vulgaris* seedling selection.

*Male, or pollen, parent.*—Unnamed and unpatented proprietary *Primula vulgaris* seedling selection.

Propagation:

*Type.*—By tissue culture.

*Time to initiate roots.*—About four weeks at 20° C.

*Time to produce a rooted young plant.*—About five weeks at 20° C.

*Root description.*—Fibrous; white in color.

*Rooting habit.*—Freely branching.

Plant description:

*Plant form/habit.*—Upright, compact, and uniform plant habit. Vigorous growth habit. Leaves basal.

*Plant height.*—About 10 cm to 14 cm, average 12.2 cm.

*Plant diameter.*—About 22 cm to 27 cm, average 24.6 cm.

*Foliage description.*—Arrangement: Basal, simple. Length: About 18 cm. Width: About 7 cm. Shape: Oblanceolate. Apex: Obtuse, tip blunt. Base: Acute. Margin: Slightly wavy. Texture, upper surface: Smooth. Texture, lower surface: Prominent venation; pubescent. Venation pattern: Pinnate. Color: Developing leaves, upper surface: Slightly darker than 144A. Developing leaves, lower surface: 146B. Fully expanded leaves, upper surface: Between 137C and 146C. Fully expanded leaves, lower surface: Between 137C and 146C. Venation, upper surface: 145C flushed with 63B near base of leaf. Venation, lower surface: 147D. Petiole: Sessile leaf.

Flower description:

*Flower type/habit.*—Single, rounded, double flower; flowers face upright and outward. Freely flowering habit with about 18–30, averaging 23, flower buds and flowers per plant.

*Fragrance.*—None.

*Natural flowering season.*—Recurrent flowering during the spring in the United Kingdom. Flowers persistent.

*Flower buds.*—Height: About 1.3 cm. Diameter: About 9 cm to 12 mm, average 10.3 mm. Shape: Broadly ovoid. Color: 144B.

*Flower diameter.*—About 32 mm to 35 mm, larger when fully opening in spring.

*Flower depth.*—About 9.7 mm to 13 mm.

*Petals.*—Quantity per flower: About 21 to 34 in several concentric whorls around petaloids. Length (from throat): Approximately 19 mm to 23 mm. Arrangement: Fused at base. Width: 10.5 mm to 23.5 mm, averaging 14.4 mm; difficult to measure due to fusing of petals. Shape: Obovate, with variable fringe and outer edge. Apex: Blunt, occasionally incised to varying degrees. Margin: Entire, with irregular fringe at tip. Texture, upper and lower surfaces, and throat: Smooth. Tube texture: Smooth, beneath calyx. Color: Developing petals, upper surface: 1D. Developing petals, lower surface: 155A to 1D. Fully open petals, upper surface: 1D to 2D, blotches of 9A at base, with petals fading to between 2D and 3D. Fully open petals, lower surface: 2D.

*Petaloids.*—Appearance: Very similar to petals. Arrangement: Concentric. Number: 10–18, average 13–14. Shape: Similar to petals; fused and overlapping. Length: Variable, from 11.5 to 20.3 mm., average 16 mm. Width: Extremely variable, from 6–7 to 15.5 mm., average 10.7 mm. Texture: Smooth, both upper and lower sides. Color: Immature 3A, mature 3D.

*Sepals.*—Quantity per flower: Typically, five in a single whorl, fused for 40% of length. Length: About 13.8 mm to 16.5 mm, greater in spring when flowers are just fully expanded. Width: About 5.5 cm to 8.1 cm. Shape: Broad, elliptic. Apex: Obtuse, ruffled. Margin: Wavy. Texture, upper surface: Smooth. Texture, lower surface: Hirsute, mostly on veins. Color, upper surface: 144A. Color, lower surface: 144B.

*Peduncles.*—Length: About 7 cm to 9 cm. Diameter: About 2 mm to 3 mm. Orientation: Mostly erect. Strength: Strong. Texture: Slightly pubescent. Color: 181C to 181D.

*Reproduction.*—'Kerbelmilk' is sterile.

Disease/pest resistance: Plants of 'Kerbelmilk' have not shown a greater susceptibility to pathogens and pests common to *Primula.*

Temperature tolerance: Plants of the new *Primula* have been observed to tolerate limited periods of exposure to temperatures from about −5° C. to 28° C.

It is claimed:

1. A new and distinct cultivar of *Primula* plant named 'Kerbelmilk,' as illustrated and described.

* * * * *

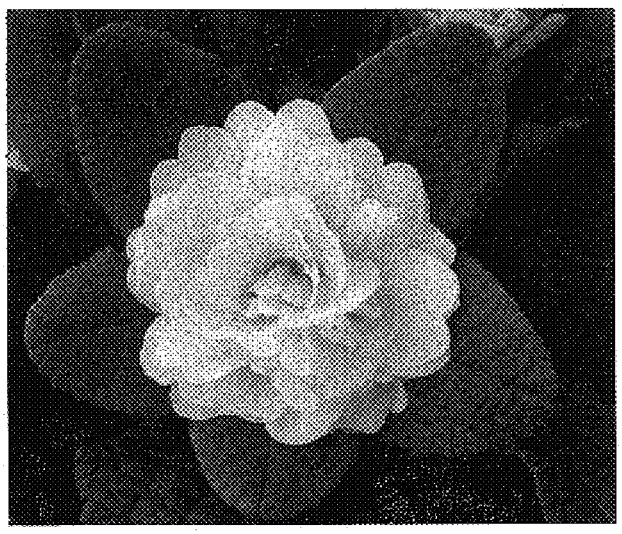

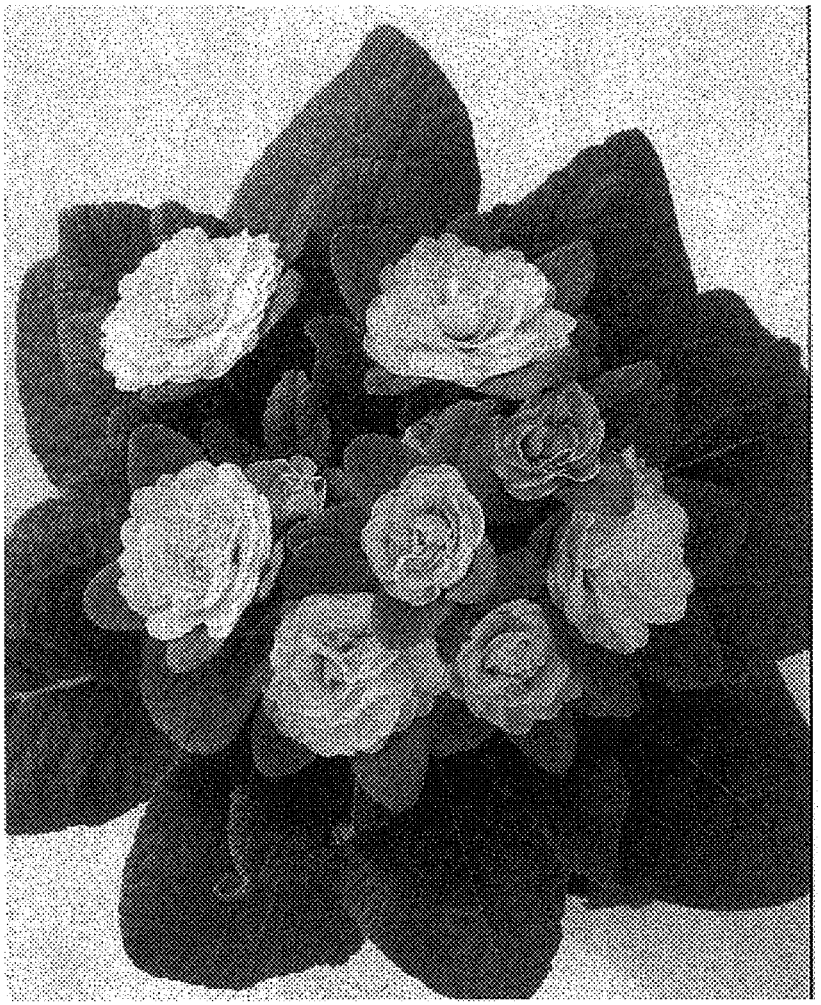
Primula Kerbelmilk DW & PG Kerley